US008308702B2

(12) United States Patent
Batchvarova et al.

(10) Patent No.: US 8,308,702 B2

(45) Date of Patent: Nov. 13, 2012

(54) FOAMING POROUS PAD FOR USE WITH A MOTORIZED DEVICE

(75) Inventors: Nikoleta Batchvarova, Princeton Junction, NJ (US); David Gubernick, Cherry Hill, NJ (US); Mark Murphy, Flemington, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 12/764,479

(22) Filed: Apr. 21, 2010

(65) Prior Publication Data

US 2011/0258791 A1 Oct. 27, 2011

(51) Int. Cl.
*A61H 33/04* (2006.01)
*A61M 35/00* (2006.01)

(52) U.S. Cl. .......................... 604/303; 604/289; 604/290

(58) Field of Classification Search .......... 604/289–290, 604/303, 305
See application file for complete search history.

(56) References Cited

U.S. PATENT DOCUMENTS

| | | | | |
|---|---|---|---|---|
| 3,472,242 | A * | 10/1969 | Demner | 132/333 |
| 4,159,883 | A | 7/1979 | Mizell | |
| 4,673,525 | A * | 6/1987 | Small et al. | 510/151 |
| 5,439,487 | A | 8/1995 | Stanitzok | |
| 6,090,085 | A * | 7/2000 | Mehl et al. | 604/291 |
| 6,257,785 | B1 * | 7/2001 | Otten et al. | 401/7 |
| 7,306,569 | B2 | 12/2007 | LaJoie et al. | |
| 2003/0008588 | A1 * | 1/2003 | Kohlruss et al. | 442/341 |
| 2005/0043653 | A1 * | 2/2005 | Trimmer et al. | 601/1 |
| 2006/0099380 | A1 | 5/2006 | Vollmert et al. | |
| 2006/0141014 | A1 | 6/2006 | Eknoian et al. | |
| 2006/0247585 | A1 * | 11/2006 | Kelly | 604/290 |
| 2007/0010828 | A1 | 1/2007 | Eknoian et al. | |
| 2007/0094827 | A1 * | 5/2007 | Kilkenny et al. | 15/209.1 |
| 2008/0026177 | A1 | 1/2008 | Vollmert | |
| 2008/0052866 | A1 | 3/2008 | Matsumoto et al. | |
| 2010/0168626 | A1 | 7/2010 | Gubernick et al. | |
| 2010/0198119 | A1 | 8/2010 | Gubernick et al. | |

FOREIGN PATENT DOCUMENTS

| | | | |
|---|---|---|---|
| EP | 1350456 | A | 10/2003 |
| WO | WO 2004/052275 | A | 6/2004 |
| WO | WO 2004/058214 | A | 7/2004 |
| WO | WO 2006/005625 | A | 1/2006 |
| WO | 2008/052152 | A2 * | 5/2008 |
| WO | WO 2008/134911 | A | 11/2008 |

* cited by examiner

*Primary Examiner* — Michele M Kidwell

(57) ABSTRACT

A foaming porous pad suitable for coupling to a hand-held device and for application to human skin includes a porous pad substrate and a foaming composition disposed on the porous pad substrate. The porous pad substrate includes a nonwoven pile fabric having a nonwoven backing layer and a pile comprising individual fibers extending from the backing layer. The nonwoven pile fabric has fibers having a denier of less than about 9. Other aspects of the disclosure include a kit including a foaming porous pad and a motorized handheld device, methods of making the foaming porous pad, and methods of using the foaming porous pad.

5 Claims, 4 Drawing Sheets

FOAMING POROUS PAD FOR USE WITH A MOTORIZED DEVICE

FIELD OF THE INVENTION

The present invention relates to a foaming porous pad for use with a motorized device, and more particularly, to a foaming porous pad having a multi-layer configuration for providing increased foaming for various skin care applications such as cleansing and exfoliating and topical agents' deposition.

BACKGROUND OF THE INVENTION

Various treatment for the skin are proposed for cleansing, exfoliating or even eliminating common skin ailments (oiliness, dryness, pores, age spots, blotches, darkening, uneven tone, and the like), acne and other chronic skin problems typically associated with skin aging or environmental damage to human skin. Such treatments range from application of specialty cosmetics such as packs and masks, oral intake of vitamins, to chemical peeling, laser surgery, photofacial, and others. These skin treatments may facilitate the delivery and deposition of benefit agents to skin tissue, e.g., cleansing and the delivery of acne treatment compositions or rejuvenating agents such as retinol. Though seldom life threatening, skin health issues can be uncomfortable and may cause chronic disabilities. In addition, because the skin is so visible, skin health issues and cosmetic skin conditions can lead to psychological stress in the patients who have them. These factors have driven people to seek improved solutions to health care and skin care.

Substrate-based skin care devices, such as pads, are increasing in popularity as a slightly elaborate, but effective means of providing special treatment at the consumer's home. Generally, the consumer expects relatively high efficacy from these products. When such substrate-based skin care device is applied to a certain area of the skin, the substrate may generate a foam or lather. While such substrate may produce foam for cleansing, it may not produce the desired amount of foam in a short amount of time initially or may not maintain a high level of foam during use. This is a problem, as consumers generally perceive that decreased foam volume indicates decreased cleansing ability. From the standpoint of skin cleansing via a substrate-based skin care device, a foaming pad that generates sufficient foam in a short amount of time is desired.

Based on the foregoing, there is a need for a substrate-based skin care device which provides improved foaming, while also quickly providing useful skin benefits when applied to the skin. Specifically, there is a need for a substrate-based skin care device which provides skin cleansing, exfoliating and/or soothing properties.

SUMMARY OF THE INVENTION

Surprisingly, we have found a novel way to address the problem of poor foam formation in a substrate-based skin care device. In one aspect of the invention, a foaming porous pad suitable for coupling to a hand-held device and for application to human skin includes a porous pad substrate and a foaming composition disposed on the porous pad substrate. The porous pad substrate includes a nonwoven pile fabric having a nonwoven backing layer and a pile comprising individual fibers extending from the backing layer. The nonwoven pile fabric has fibers having a denier of less than about 9.

In another aspect of the invention, a kit includes a motorized handheld device and a foaming porous pad. The motorized handheld device has a body and an attachment surface arranged and configured for disposition toward human skin. The foaming porous pad includes about 50 to about 25 wt-% of a porous pad substrate and about 50 to about 75 wt-% of a foaming composition disposed on the porous pad substrate. The porous pad substrate includes a nonwoven pile fabric having a nonwoven backing layer and a pile comprising individual fibers extending from the backing layer. The nonwoven pile fabric has fibers having a denier of less than about 9. The foaming porous pad is arranged and configured for coupling to the attachment surface of the hand-held device with the pile of the nonwoven pile fabric disposed toward the human skin during use.

In yet another aspect of the invention, a method of making foaming porous pads includes forming a nonwoven pile fabric, applying a foaming composition to the nonwoven pile fabric, separating individual porous pads from the nonwoven pile fabric, and packaging a plurality of individual porous pads. The foaming porous pads are suitable for coupling to a hand-held device and for application to human skin.

The nonwoven pile fabric in this aspect of the invention is formed by needlepunching at least one carded web of individual fibers to form a substantially integrated, planar web of fibers primarily oriented in the plane of the web and needlepunching the substantially integrated, planar web of fibers to form a pile comprising individual fibers extending from a backing layer. The fibers of the nonwoven pile fabric have a denier of less than about 9, and the fibers of the backing layer remain primarily oriented in the plane of the web. The foaming composition may be applied either before or after the individual porous pads are separated from the nonwoven pile fabric.

In yet another aspect of the invention, a method of caring for human skin includes coupling a foaming porous pad to an attachment surface of a motorized handheld device, wetting the foaming porous pad, activating the motorized handheld device to generate motion of the foaming porous pad, applying the foaming porous pad to human skin, and moving the foaming porous pad about the human skin. The foaming porous pad includes about 50 to about 25 wt-% of a porous pad substrate and about 50 to about 75 wt-% of a foaming composition disposed on the porous pad substrate. The porous pad substrate has a nonwoven pile fabric including a nonwoven backing layer and a pile comprising individual fibers extending from the backing layer. The nonwoven pile fabric has fibers having a denier of less than about 9. The foaming porous pad is arranged and configured for coupling to the attachment surface of the motorized handheld device with the pile of the nonwoven pile fabric disposed toward the human skin during use.

These and other features, aspects, and advantages of the present invention will become evident to those skilled in the art from a reading of the present disclosure with the appended claims.

DETAILED DESCRIPTION OF THE INVENTION

Figure 1:
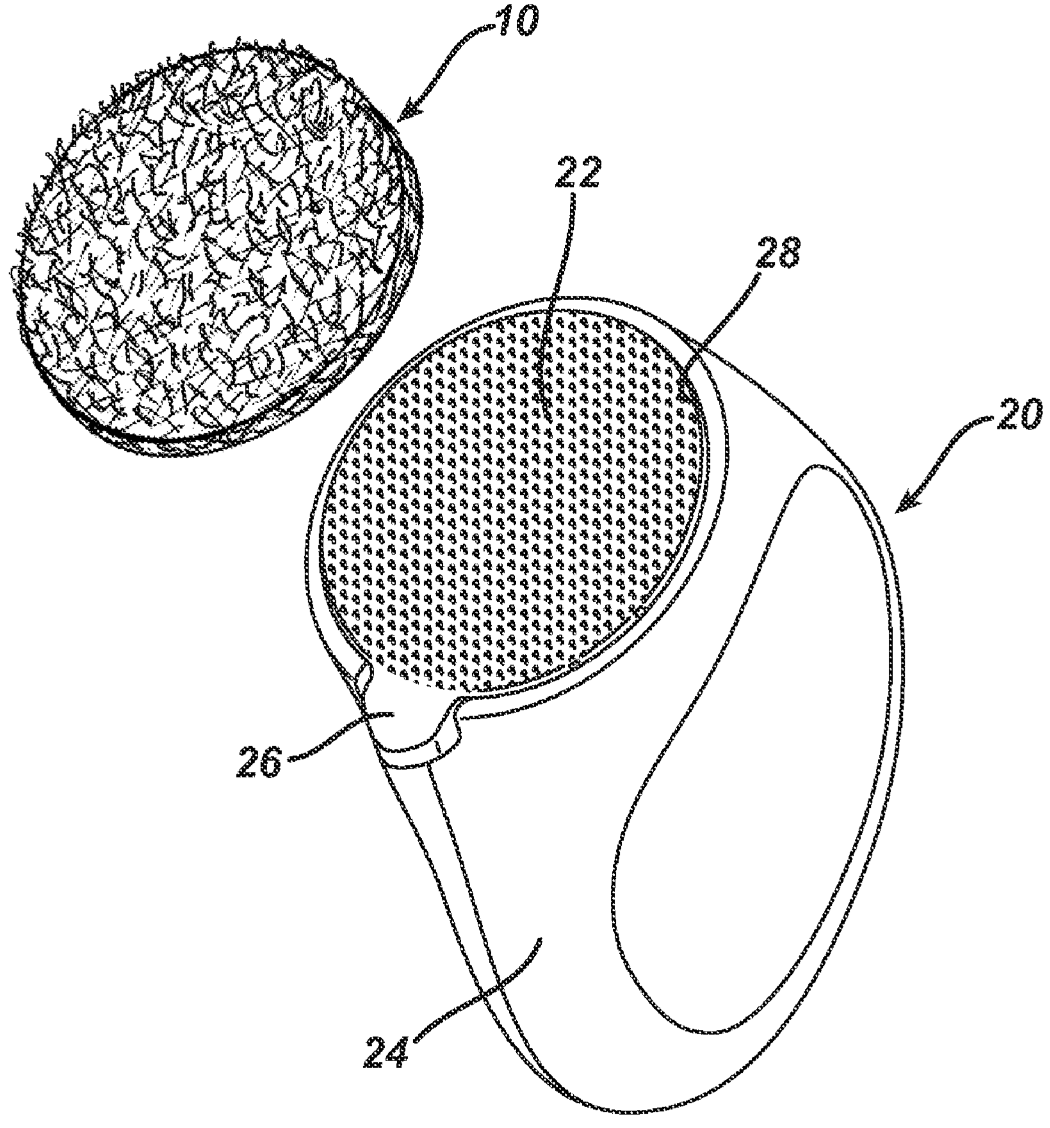
FIG. 1 is a perspective view of a foaming porous pad and hand-held device useful in the practice of the present invention.

It is believed that one skilled in the art can, based upon the description herein, utilize the present invention to its fullest extent. The following specific embodiments are to be construed as merely illustrative and not limiting the remainder of the disclosure in any way whatsoever.

As used herein the specification and the claims, the term "exfoliation" and variants thereof relate to the peeling and sloughing off of the skin's tissue cells.

As used herein the specification and the claims, the term "cleansing" and variants thereof relate to removal of dirt, oils, and the like from the surface of the skin, especially through surfactant washing, and perhaps also penetrating into the pores of the skin. In "abrasive cleansing," some degree of exfoliation also occurs.

As used herein the specification and the claims, the term "nonwoven" and variants thereof relate to a sheet, web, or bat of natural and/or man-made fibers or filaments, excluding paper, that have not been converted into yarns (hereafter "individual fibers"), and that are bonded to each other by any of several means. For additional clarification, nonwovens are distinct from woven and knitted fabrics. The fibers included in the nonwoven materials may be staple or continuous or be formed in situ, and preferably, at least about 50% of the fibrous mass is provided by fibers having a length to diameter ratio greater than about 300:1.

As used herein the specification and the claims, the term "pile fabric" and variants thereof relate to a fabric with fiber ends or uncut fiber loops which stand up densely on the surface.

As used herein the specification and the claims, the term "pile" and variants thereof relate to the layer of a fabric that has fiber ends or uncut fiber loops that stand up densely on one surface of the fabric.

Briefly described, in a preferred embodiment, the present invention overcomes the disadvantages mentioned in the background portion of the present application and meets the recognized need for such a substrate base skin care system by providing a pile fabric, porous pad substrate, comprising a backing layer and a pile extending from the backing layer. A foaming composition is applied to the porous pad substrate, and a plurality of the foaming porous pads is packaged until use. The backing layer provides integrity to the nonwoven pile fabric, and the pile provides a structure that is capable of generating high foam levels when the foaming composition is wetted and worked against the skin by a motorized system and/or by manual means of the user.

Accordingly, the present invention is directed to systems, articles, compositions, and methods useful for generating a sufficient and long lasting amount of foam from a porous pad substrate employing a motorized applicator. In various embodiments of the invention, such systems, articles, and methods provide a unique combination of high reliability and convenience for the user, as well as a highly efficacious foaming porous pad.

Porous Pad Substrate

According to its major aspects and broadly stated, the present invention in its preferred form is a nonwoven pile fabric comprising a backing layer, a pile extending from the backing layer, and a foaming composition. The backing layer preferably has a higher fiber density than the pile, has fibers predominantly oriented in an x-y plane (the plane of the backing layer), and provides a contacting surface for attachment to a hand-held device. The pile is less dense than the backing layer and has fibers extending out of and away from the backing layer.

This structure enables the pad to generate the desired amount foam quickly and to maintain a sufficient volume of foam during use. This foaming action can be accomplished with a minimal amount of water applied by the user.

A wide variety of materials can be used as the porous pad substrate. Examples of suitable substrates include, but are not limited to, non-woven fabrics such as needle-punched fabrics, hydro-entangled fabrics, high-loft fabrics, or other entangled fiber fabrics.

The porous pad substrate is preferably formed to retain a foaming composition (such as by absorbing the foaming composition among, along, and/or between fibers of the porous pad substrate) for a period of time at least as long as from when the product is manufactured to a time when the product is used by a consumer (i.e., a shelf storage period). In this embodiment of the invention, during this shelf storage period the porous pad substrate of the foaming porous pad should generally maintain its mechanical integrity such that a user can apply the foaming porous pad to a motorized applicator and work the foaming composition onto the skin.

FIG. 1 depicts an embodiment of a foaming porous pad consistent with embodiments of the invention described herein and a hand-held device. Foaming porous pad 10 is generally sized and shaped to lie against the motorized applicator 20 and to bear against the skin of a user. It is preferred that the foaming porous pad 10 is conformable to an applicator surface 22 of the motorized applicator 20, i.e., the foaming porous pad 10 is capable of being placed on the applicator surface 22 and generally conforming to the shape of the applicator. The pad 10 generally only requires simple manipulation such as unfolding or at most slight tearing along preformed perforations in order to assume a form that can move efficiently on a human face. In a preferred embodiment, the pad 10 is oriented to be placed on the motorized applicator with the backing layer 12 adjacent the applicator surface 22 and the pile 14 directed toward the skin of the user.

Figure 2:
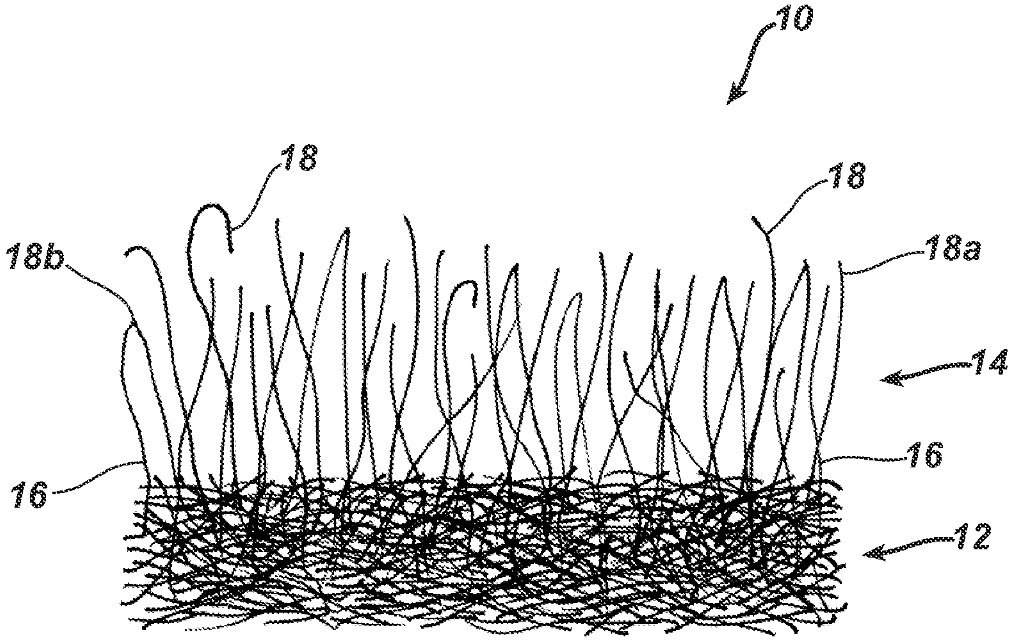
FIG. 2 is a cross-section of the foaming porous pad taken along line 2-2 of FIG. 1.

As shown in more detail in FIG. 2, a proximal end 16 of the fibers of the pile 14 is secured to and extends from the backing layer 12. Distal portions 18 of the fibers of the pile 14 are spaced from the backing layer 12 and are generally free to move with respect to adjacent fibers. The distal portion 18 of a fiber may be in the form of a free end **18*a* of the fiber, that is, the fiber extends out of the backing layer and terminates in a free end 18*a* disposed at a distance from the backing layer 12. Alternatively, the distal portion 18*b* of a fiber may be a middle portion of a loop; the fiber may extend out of and away from the backing layer 12 to the middle portion of a loop of the fiber and return to the backing layer 12**.

Preferably, the backing layer 12 has a higher density than the pile 14. In this embodiment of the invention, the backing layer and pile have a layer thickness ratio of about 1.0:1.1 to about 1.0:1.5 and a preferred ratio of about 1.0:1.2. The backing layer 12 has a higher density than the pile 14; the backing layer 12 has a density from about 50 g/($m^2$*mm) to about 80 g/($m^2$*mm) and the pile 14 has a density from about 30 g/($m^2$*mm) to about 60 g/($m^2$*mm). Preferably the backing layer 12 has a density from about 60 g/($m^2$*mm) to about 70 g/($m^2$*mm) and the pile 14 has a density from about 40 g/($m^2$*mm) to about 50 g/($m^2$*mm).

Figure 3:
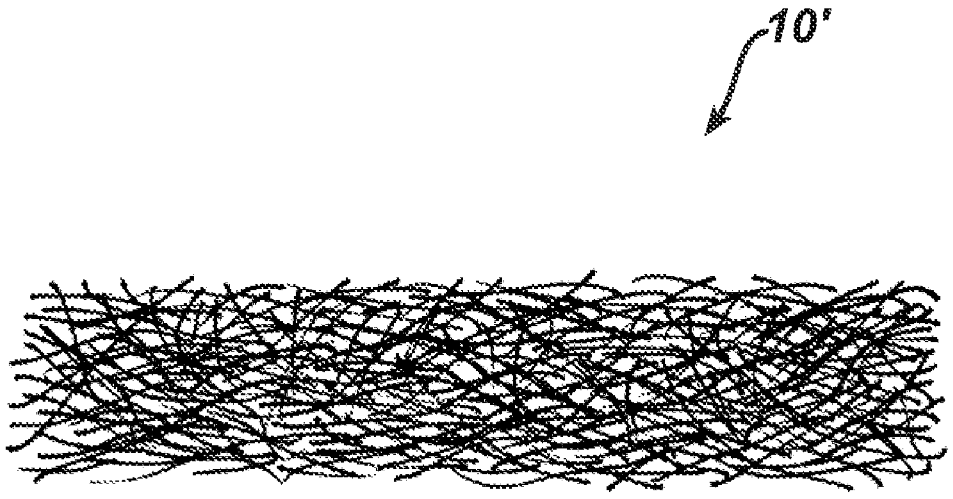
FIG. 3 PRIOR ART
FIG. 3 is a cross-section of a needlepunched nonwoven porous pad according to the prior art.

The nonwoven pile fabric of the present invention differs from the pads 10' of the prior art having the cross-section shown in FIG. 3. Prior art pads, such as DEEP CLEAN foaming pads used in the NEUTROGENA® WAVE™ power cleanser, are nonwoven needlepunched fabrics that lack the enhanced foam-generating properties of the pile in the present invention.

Non-woven substrates may be comprised of a variety of natural and/or synthetic materials. By “natural” it is meant that the materials are derived from plants, animals, insects, or byproducts of plants, animals, and insects. By “synthetic” it is meant that the materials are obtained primarily from various man-made materials or from natural materials, which have been further altered. Non-limiting examples of natural materials useful in the present invention are silk fibers, keratin fibers (such as wool fibers, camel hair fibers) and cellulosic fibers (such as wood pulp fibers, cotton fibers, hemp fibers, jute fibers, and flax fibers).

Examples of synthetic materials include, but are not limited to, those selected from the group containing acetate fibers, acrylic fibers, cellulose ester fibers, cotton fibers, polyamide fibers, polyester fibers, polyolefin fibers, polyvinyl alcohol fibers, rayon fibers, polyurethane foam, and mixtures thereof. Preferred substrates include nonwoven webs of polyester fibers and nonwoven webs of blends of polyester and polyolefin (such as polypropylene) fibers.

Substrates made from one or more of the natural and synthetic materials useful in the present invention can be obtained from a wide variety of commercial sources such as Freudenberg & Co. (Durham, N.C. USA), BBA Nonwovens (Nashville, Tenn. USA), PGI Nonwovens (North Charleston, S.C. USA), Buckeye Technologies/Walkisoft (Memphis, Tenn. USA), Sansho Shigyo K.K. (Tosa City, Kouchi, Japan), and Fort James Corporation (Deerfield, Ill. USA).

Methods of making non-woven substrates are also well known in the art. Such methods include, but are not limited to, air-laying, water-laying, melt-blowing, spin-bonding, or carding processes. The resulting substrate, regardless of its method of production or composition, is then generally subjected to at least one of several types of bonding operations to anchor the individual fibers together to form a self-sustaining web. The non-woven substrate can be prepared by a variety of processes including needle punched-entanglement, hydro-entanglement, thermally bonding, chemical bonding and combinations of these processes. Moreover, the substrates can have a single layer or multiple layers. In addition, a multi-layered substrate can include film layer(s) (e.g., aperture or non-aperture film layers) and other non-fibrous materials.

Nonwoven materials of increased strength can also be obtained by using the so-called spunlace or hydro-entanglement technique. In this technique, the individual fibers are entangled so that an acceptable strength or firmness is obtained without the need to use binding materials. The advantage of the latter technique is the excellent softness of the non-woven material. Additives may also be added in order to increase the softness of the substrates. Examples of such additives include, but are not limited to, polyols such as glycerol, propylene glycol and polyethylene glycol, phthalate derivatives, citric esters, surfactants such as polyoxyethylene (20) sorbitan esters, and acetylated monoglycerides.

Preferred nonwoven materials of the present invention are needlepunched nonwovens. More preferably, the nonwovens are dilour processed to form the pile. This process can provide loops and unlooped fiber ends in the pile.

The existence of loops or fiber ends in the pile is influenced by a number of factors in the production of the nonwoven pile fabric. These factors include the length of the fibers in the fabric, and the type of needles used in the needlepunching steps, especially the pile-forming step. The needles may be selected to create a large number of cut fibers in the pile, leaving free ends, or they may be selected to reduce the number of fibers cut, providing a greater proportion of looped fibers in the pile.

The fibers of the porous pad substrate have a relatively low denier. If the fibers are too large in cross-section, they will be too stiff and uncomfortable for use on human skin. If the fibers are too small, the fibers will lie down against the backing layer and become matted. The resulting porous pad substrate will not provide the high-foaming characteristics desired. Preferably, the fibers have a denier of up to about 9. More preferably, at least about 90 wt-% of the fibers have a denier of up to about 6.

In a preferred embodiment, the porous pad substrate has a blend of fibers having a denier of up to about 6, and more preferably, a blend of fibers having a denier of about 3 and about 6. In one blend, about 90 to about 50 wt-% of a smaller fiber and about 10 to about 50 wt-% of a larger fiber are blended. Preferred smaller fibers have a denier of about 1.5 to about 4, more preferably about 3. Preferred larger fibers have a denier of about 4.5 to about 9, more preferably about 6.

The basis weight of the porous pad substrate may range from about 170 grams per square meter (gsm) to about 380 gsm, such as between about 200 gsm and about 350 gsm, more preferably between about 225 gsm and about 300 gsm. The porous pad substrate may have an average thickness that is about 2.5 mm, such as between about 1.5 mm and about 3.5 mm.

With an average thickness of between about 1.5 mm and about 3.5 mm and the ratio of backing layer and pile thickness of about 1.0:1.1 to about 1.0:1.5, the thickness of the pile is between about 0.8 mm and about 2.1 mm. Thus, the ratio of the fiber length extending in the pile to the fiber diameter (the “aspect ratio”) of the fibers extending in the pile is about 35 to about 150. It will be recognized that the lowest aspect ratio will occur with 9 denier polyethylene fibers in a pad having a thickness of 1.5 mm and a ratio of backing layer to pile of 1.0:1.1, and the highest aspect ratio will occur with 3 denier polyester fibers in a pad having a thickness of 3.5 mm and a ratio of backing layer to pile of 1.0:1.5. Thus, the aspect ratio of the fibers extending in the pile is from about 21 to about 120.

Sensory attributes may also be incorporated to the porous substrates. Examples of such sensory attributes include, but are not limited to color, texture, pattern, and embossing of the substrate.

Foaming Composition

The foaming porous pad includes a foaming composition, such as may be used to enhance the foaming capacity of the pad. Examples of skin treatment articles with foaming compositions are shown in Eknoian et al., US Pat. App. No. 2006/0141014, the disclosure of which is incorporated by reference herein.

The foaming composition comprises one or more surfactants. The surfactants are preferably lathering surfactants. As used herein, “lathering surfactant” means a surfactant, which when combined with water and mechanically agitated, generates a foam or lather. Such surfactants are preferred since increased lather is important to consumers as an indication of cleansing effectiveness. In certain embodiments, the surfactants or combinations of surfactants are mild. As used herein, “mild” means that the surfactants as well as to the articles of the present invention demonstrate skin mildness comparable to a mild alkyl glyceryl ether sulfonate (AGS) surfactant based synthetic bar, i.e., synbar. Methods for measuring mildness, or inversely the irritancy, of surfactant containing articles, are based on a skin barrier destruction test. In this test, the milder the surfactant, the lesser the skin barrier is destroyed. Skin barrier destruction is measured by the relative amount of radio-labeled (tritium labeled) water ($3H-H_2O$) which passes from the test solution through the skin epidermis into the physiological buffer contained in the diffusate chamber. This test is described by T. J. Franz in the *J. Invest. Dermatol.,* 1975, 64, pp. 190-195; and in U.S. Pat. No. 4,673,525, to Small et al., issued Jun. 16, 1987. Other testing methodologies for determining surfactant mildness well known to one skilled in the art can also be used.

A wide variety of lathering surfactants are useful herein and include those selected from the group consisting of anionic lathering surfactants, nonionic lathering surfactants, cationic lathering surfactants, amphoteric lathering surfactants, and mixtures thereof.

In one embodiment of the invention, the foaming composition is present in an amount sufficient to generate foam (according to the "Foam Test" described below in the Example Section) in less than 14 seconds, and preferably in less than about 12 seconds, and more preferably in less than about 11 seconds, after being activated by a liquid. The foaming composition preferably generates foam of sufficient quantity and to last about for at least about 2 minutes.

In order that the foaming porous pad provides a desired amount of foaming, the foaming composition is preferably present at least about 50 wt-% of the foaming porous pad. In other words, a dry porous pad substrate weighing 1 g would have applied thereto about 1 g of the foaming composition. More preferably the foaming agent is present in an amount that is between about 50 and about 75 wt-% of the foaming porous pad, and the porous pad substrate may be present at about 50 to about 25 wt-% of the foaming porous pad. Most preferably, the foaming agent is present at between about 60 and about 70 wt-% of the foaming porous pad, and the porous pad substrate is present at between about 40 and about 30 wt-% of the foaming porous pad. By having the foaming composition present in this amount, the foaming composition may be readily worked on skin placed in contact with the foaming porous pad as well as provide sufficient foaming when dosed with an appropriate amount of water by the user.

Motorized Handheld Device

The motorized handheld device 20 is arranged and configured to impart motion to skin placed in contact therewith (indirectly through the foaming porous pad. The motorized handheld device 20 includes a body 24 and an attachment surface 22 suitable for coupling the foaming porous pad thereto. The motorized handheld device 20 further has a motor within the body 24 and a means for transferring mechanical energy from the motor to the attachment surface 22 in order to impart motion to a surface of a foaming porous pad coupled thereto. In a preferred embodiment, a coupler 26 fits into a receptacle 28 on the body 24 of the motorized handheld device 20. In such embodiments, the coupler 26 provides the attachment surface 22 that can engage a surface of the foaming porous pad, such as a plurality of hooks of a hook-and-loop fastener system. The hooks can then engage fibers, for example, fibers of the backing layer of the foaming porous pad. The motion generated by the applicator may include but is not limited to rotary, oscillating, vibrating or a combination thereof. Examples of useful motorized handheld devices 20 are disclosed in Gubernick et al., U.S. Ser. Nos. 12/178,946 and 12/178,780, the contents of which are hereby incorporated by reference.

Benefit Agents

In one embodiment of the invention, the foaming porous pad includes one or more benefit agents. What is meant by an "benefit agent" is a compound (e.g., a synthetic compound or a compound isolated from a natural source) that has a cosmetic or therapeutic effect on the skin including, but not limited to, lightening agents, darkening agents such as self-tanning agents, anti-acne agents, shine control agents, anti-microbial agents, anti-inflammatory agents, antifungals, anti-parasite agents, external analgesics, sunscreens, photoprotectors, antioxidants, keratolytic and exfoliating agents, surfactants, moisturizers, nutrients, vitamins, energy enhancers, anti-perspiration agents, astringents, deodorants, hair growth inhibitors, anti hair-loss agents, hair growth promoters, hair removers, skin-firming agents, anti-callous agents, anti-aging agents such as anti-wrinkle agents, skin conditioning agents, allergy inhibitors, antiseptics, external analgesics, antipruritics, antihistamines, antiinfectives, anticholinergics, vasoconstrictors, vasodilators, wound-healing promoters, peptides, polypeptides, proteins, deodorants, antiperspirants, film-forming polymers, counterirritants, enzymes, enzyme inhibitors, poison ivy treatment agents, poison oak treatment agent, burn treatment agents; anti-diaper rash treatment agents; prickly heat agents; herbal extracts; flavenoids; sensates; anti-oxidants, keratolytics; sunscreens; and anti-edema agents; and combinations thereof.

In one embodiment of the invention, the benefit agent is selected from, but not limited to, hydroxy acids, benzoyl peroxide, sulfur resorcinol, ascorbic acid and its derivatives, D-panthenol, hydroquinone, octyl methoxycinnimate, titanium dioxide, octyl salicylate, homosalate, avobenzone, polyphenolics, carotenoids, free radical scavengers, spin traps, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper, coenzyme Q10, lipoic acid, amino acids such a proline and tyrosine, lipo amino acids such as capryloyl glycine and sarcosine, vitamins, lactobionic acid, acetyl-coenzyme A, niacin, riboflavin, thiamin, ribose, electron transporters such as NADH and FADH2, and other botanical extracts, and salt, esters, and derivatives thereof. The benefit agent will typically be present in an amount of from about 0.001% to about 20% by weight of the liquid impregnate, e.g., about 0.01% to about 10% such as about 0.1% to about 5%.

Examples of vitamins include, but are not limited to, vitamin A, a vitamin B such as vitamin $B_3$, vitamin $B_5$, and vitamin $B_{12}$, vitamin C, vitamin K, and vitamin E, and salts, esters, and derivatives thereof (e.g., retinyl palmitate, ascorbyl acetate, and tocopherol acetate).

Examples of hydroxy acids include, but are not limited, to glycolic acid, lactic acid, malic acid, salicylic acid, citric acid, and tartaric acid.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbic acid glucoside, magnesium ascorbyl phosphate, and ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isofavonoids and their derivatives (e.g., genistein and diadzein), extracts containing resveratrol and the like. Examples of such natural extracts include grape seed, green tea, pine bark, and propolis.

Examples of botanical extracts include, but are not limited to legumes such as Soy, Aloe Vera, Feverfew, Hedychium, Rhubarb, Portulaca, Cedar Tree, Cinnamon, Witch Hazel, Dandelion, Chinese Angelica, Turmeric, Ginger, Burnet, Houttuynia, Coix Seed, and Thyme. What is meant by a "botanical extract" is a blend of two or more compounds isolated from a plant.

In one embodiment of the invention, the benefit agent is designed for application on the forehead region and includes, but is not limited to: oil-control agents such as titanium dioxides, alcohols, botanical extracts, and talc; pore refining agents such as alpha-hydroxy acids, beta-hydroxy acids, and enzymes; anti-acne agents such as benzoyl peroxide, salicylic acid, trichlorcarban, triclosan, azelaic acid, clindamycin, adapalene, erythromycin, sodium sulfacetamide, retinoic acid, and sulfur; oil-absorbing agents such as titanium dioxides and clays; shine control agents such as silicones, alcohols, talc, and clays; dark spot reduction agents such as vitamin C, hydroquinone, botanical extracts, alpha-hydroxy acids, beta-hydroxy acids, and retinoids; and/or wrinkle/fine-line reduction agents such as retinoids, alpha-hydroxy acids, and enzymes.

In another embodiment of the invention, the benefit agent is designed for application around the mouth and includes, but is not limited to: hydration/moisturization agents such a glycerin, silicone, glycols, botanical extracts, and esters; pore-refining agents; anti-acne agents; vasodilators such as niacinamide and horsechesnut extract; vasoconstrictors such as caffeine and botanical extracts; skin-lifting agents such as (e.g., copper containing peptides, dimethyaminoethanol, and polymers); skin-firming polymers; wrinkle/fine-line reduction agents; depigmenting/skin lightening agents such as vitamin C, hydroquinone, botanical extracts, alpha-hydroxy acids, beta-hydroxy acids, retinoids, arbutin, and kojic acid; and depilatory/hair reducing agents such as soy extracts, n-acetyl-cysteine, and isoflavones.

While various combinations are contemplated, under one non-limiting example, one or more benefit agents are selected from the group consisting of ascorbic acid and its derivatives, alpha-hydroxy-acids, beta-hydroxyacids, alkanolamines, proteins, enzymes, and enzyme activators, and combinations thereof are in the liquid impregnate, and one or more benefit agents are selected from the group consisting of retinoids, tocopherols, enzymes, enzyme activators, and combinations thereof are within the liquid core.

In one embodiment of the invention, the pad comprises an enzyme such as a lignin peroxidase and a suitable activator such as a peroxide (e.g., hydrogen peroxide) as described in WO 2004/052275.

Packaging of Product

In one embodiment of the invention, the product is in finished packaged form inside a package. In one embodiment, the package is a container such as a sealed flexible film wrapper, a tube, a tub, a pouch or a jar containing the foaming porous pad. These packages can be of plastic, metal, glass, paper and/or combinations and laminates of these materials.

In one embodiment of the invention, the product includes instructions directing the user to apply the foaming porous pad to the motorized applicator. In one embodiment, the instructions may direct the user to apply the product directly to the skin. In another embodiment, the instructions may direct the user to apply a liquid to the foaming porous pad prior to application to the skin (e.g. to add water, a toner, or a cleanser to the product).

The instructions may direct contacting the foaming porous pad with the skin (e.g., the face) for a period of time, such as from about 1 minute to about 10 minutes (e.g., such as from about 3 minute to about 7 minutes). The user may also be directed to rinse any liquid remaining on the skin after removal of the foaming porous pad.

Method of Making and Using the Product

Figure 4:
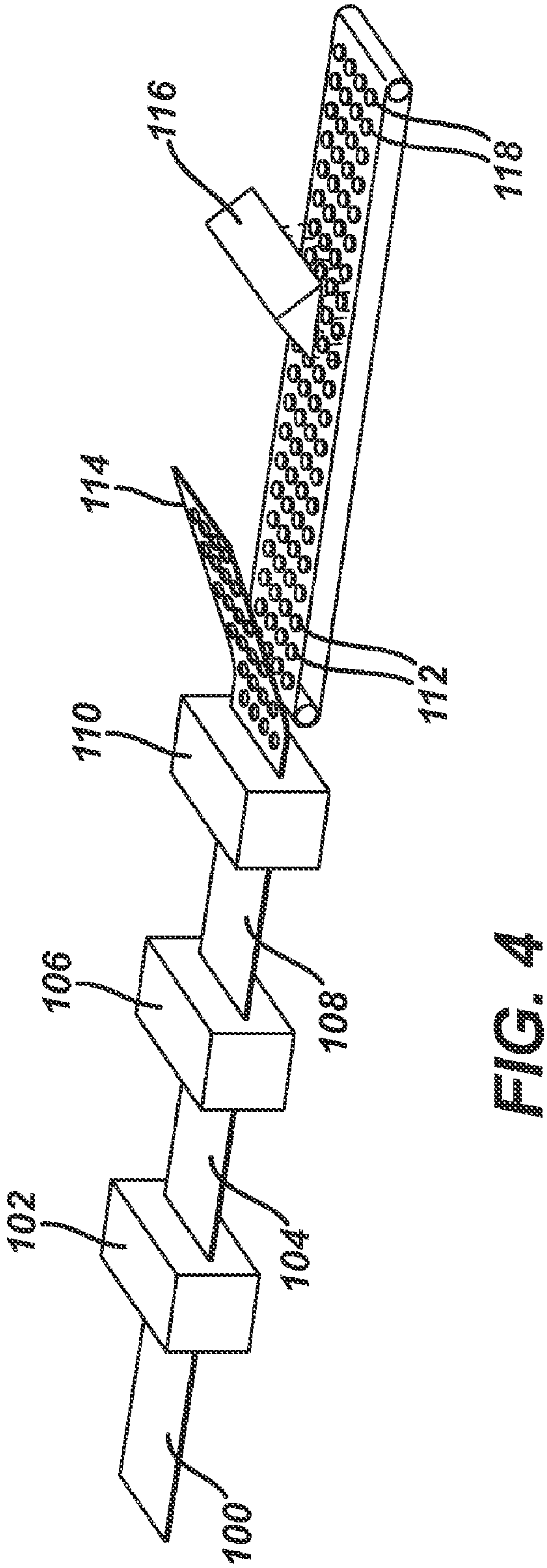
FIG. 4 is a schematic view of a method of making the foaming porous pads of the present invention.

FIG. 4 depicts elements of a standard nonwoven manufacturing device modified for making the foaming porous pad according to the present invention. One or more layers can be combined in the following process. Fibers and/or a fiber blend are chosen for each layer to meet the intent of the product and layers are independently fed into an opener and then to a blender/mixer for each layer. This fiber/fiber blend for each layer is then fed to the input side of a typical textile carding machine which forms a loose web or batt of fiber for each layer which can be cross-lapped if a wider width is needed. One or more of these layers can then be mechanically bonded through needlepunching.

As shown in FIG. 4, the web 100 is introduced to a needlepunching station 102 to form a bonded web 104. The resulting bonded web 104 is then further processed in a specialized needlepunching process, sometimes called a Dilour process (developed by Dilo AG, Germany). In this process shown schematically as station 106, the needle board of the needlepunching process incorporates needles that are designed to move fibers in only one direction, generally out from the initial needlepunched fabric web. The resulting nonwoven pile fabric 108 moves to a punching station 110 in which individual porous pad substrates 112 are punched out of the nonwoven pile fabric 108. The waste lattice 114 is removed for recycling. The porous pad substrates 112 formed of the nonwoven pile fabric can then be dosed, for example by spraying at coating station 116 to form the finished foaming porous pads 118, which can be packaged (not shown). This schematic illustration of a useful manufacturing process can, of course, be separated into several stages. For example, the bonded web 104, the nonwoven pile fabric 108, or both can be wound into rolls and stored for later processing. Alternatively, the coating station 116 can be located before the punching station 110, as desired.

EXAMPLES

Example 1

An example of the present invention is a disposable pad for use with a motorized handheld skin care applicator. The pad is formed of two layers carded fibers that are needlepunched to form a bonded web as described above.

The binderless nonwoven pile fabric is formed of a first carded layer having a basis weight of 4.3 oz/yd$^2$ (145 gsm) white/off-white layer of 100% white polyester fibers (3 denier, 3 inch (75 mm) length) and a second carded layer having a basis weight of 3.4 oz/yd$^2$ (115 gsm). The second layer is formed of nominally 60 wt-% white polyester fibers (3 denier, 3 inch (75 mm) length) and 40 wt-% blue polypropylene fibers (5.0/6.0 denier, 4 inch (100 mm) length). These carded layers are then needlepunched to form a bonded web, having a nominal basis weight of about 7.7 oz/yd$^2$ (260 gsm). This bonded web is then introduced to a dilour processing unit in which the nonwoven pile fabric is formed. This again has a nominal basis weight of about 7.7 oz/yd$^2$ (260 gsm).

Example 2

A Foaming Test was run to determine the time to onset of foam. The Foaming Test procedure is as follows:

Foaming Test:

Objective:

Quantify the onset of foaming time and to qualitatively establish quantity of foam with the Original Wave pad and the new Foaming Upgrade pad.

Equipment Used:

Gardco LINEAR MOTION TEST EQUIPMENT, Model D10V, available from Paul N. Gardner Company, Inc. (Pompano Beach, Fla., USA)

Set Up:

Configure the test unit with 500 grams of weight on the pad, pad attachment fixed to the Gardco equipment "Brush Box"

Rubbing surface is a flat rubber surface (rubber ⅛ inch thick, 15 Shore "A" durometer)

Set test unit stroke to be 10 inches and the speed to be 20 inches per second (Note: This is equivalent to one second per stroke)

Set Counter to 60 strokes—a stroke is "one motion left and one motion right"

Provide tap water at 90° F. in beaker

Procedure:

Confirm machine operation at designated speed, stroke, weight, etc.

Dip pad into water (about 1 second) and let excess water drain (Note: Pad pickup will be a function of pad fibers and structure)

Place pad on attachment and set weighted Brush Box in position

Start counter (stroke motion) and watch longitudinal edges for foam

Record counter number when foam forms a noticeable line on either side of the pad stroke (This is the time for onset of foam)

Let machine continue for the full 60 counts (strokes).

Remove weighted Brush Box and photograph the unit (This qualitatively is the amount of foam)

Repeat at least three times.

A comparison of a commercial disposable cleaning pad for use with a motion-generating handheld device (NEUTROGENA® WAVE™ power cleanser DEEP CLEAN FOAMING PADS) and an embodiment of the present invention (Nonwoven pile fabric porous pad) was made to determine the improved foam generation of the porous pad substrate of the present invention. The pads (about 40 mm diameter, having a mass of about 0.34 g) were dosed with equivalent amounts (about 0.75 g) of same cleansing composition (similar to that disclosed in Eknoian et al., US Pat. App. No. 2006/0141014), and three pads of each were tested according to the Foam Test, described above. The time to the onset of foam and relative amounts of foam were recorded (however, absolute volume of foam was not recorded). The results are shown in Table 1, below.

TABLE 1

| Property | Onset of Foam (seconds) Average | Range | Quantity of Foam[1] |
|---|---|---|---|
| NEUTROGENA ® WAVE ™ power cleanser DEEP CLEAN FOAMING PADS[2] (Comparative Example) | 17 | 14-20 | Less |
| Nonwoven pile fabric porous pad[3] (Inventive Example) | 11 | 9-12 | More |

[1]Foaming composition (glycerin, sodium laureth sulfate, PDT-8, cocamidopropyl betaine, decyl glucoside, lauryl methyl gluceth-10 hydroxypropyldimonium chloride, phenoxyethanol, methylparaben, citric acid, salicylic acid, menthol, fragrance) as described on NEUTROGENA ® WAVE ™ power cleanser DEEP CLEAN FOAMING PADS packaging

[2]Est. Water pick-up for Wave about 2.4 g

[3]Est. Water pick-up for Foaming Upgrade about 2.2 grams

A review of the data, above shows that the porous pad substrate formed of a nonwoven pile fabric provides significantly improved foaming qualities. It provides a faster onset of foam production and relatively more foam generated.

The specification, embodiments, and examples above are presented to aid in the complete and non-limiting understanding of the invention disclosed herein. Since many variations and embodiments of the invention can be made without departing from its spirit and scope, the invention resides in the claims hereinafter appended.

The invention claimed is:

1. A kit comprising a. a motorized handheld device comprising a body and an attachment surface arranged and configured for disposition toward human skin; and b. a foaming porous pad comprising:

i. about 50 to about 25 wt-% of a porous pad substrate comprising at least about 50% fibers having a length to diameter ratio of greater than about 300:1 formed into a nonwoven pile fabric comprising a nonwoven backing layer and a pile consisting essentially of individual fibers selected from the group consisting of polyesters, polyolefins, and combinations thereof and extending from the backing layer, wherein the nonwoven pile fabric comprises fibers having a denier ranging from about 3 to about 9 and an aspect ratio ranging from about 21 to about 120; and ii. about 50 to about 75 wt-% of a foaming composition disposed on the porous pad substrate, wherein the foaming composition comprises at least one lathering surfactant;

wherein the foaming porous pad is arranged and configured for coupling to the attachment surface of the handheld device with the pile of the nonwoven pile fabric disposed toward the human skin during use.

2. The kit of claim 1, wherein the attachment surface comprises a coupler disposed in a receptacle formed in the body.

3. The kit of claim 1, wherein the foaming porous pad comprises about 40 to about 30 wt-% of the porous pad substrate and about 60 to about 70 wt-% of the foaming composition.

4. The kit of claim 1, wherein the nonwoven pile fabric comprises a blend of fibers, and wherein about 90 to about 50 wt-% of the fibers have a first denier of up to about 3, and about 10 to about 50 wt-% of the fibers have a second denier, greater than the first denier and up to about 6.

5. The kit of claim 1, wherein the lathering surfactant is mild.

* * * * *